(12) United States Patent
Kim et al.

(10) Patent No.: US 7,718,835 B2
(45) Date of Patent: May 18, 2010

(54) DEHYDROGENATION PROCESS OF DIMETHYLNAPHTHALENE USING METAL CATALYST

(75) Inventors: Hyun-Soo Kim, Kyonggi-do (KR); Young-Gyo Choi, Kyonggi-do (KR); Ik-Hyun Kwon, Kyonggi-do (KR)

(73) Assignee: Hyosung Corporation, Kyonggi-do (KR)

( * ) Notice: Subject to any disclaimer, the term of this patent is extended or adjusted under 35 U.S.C. 154(b) by 689 days.

(21) Appl. No.: 11/706,404

(22) Filed: Feb. 15, 2007

(65) Prior Publication Data
US 2008/0051618 A1    Feb. 28, 2008

(30) Foreign Application Priority Data
Aug. 22, 2006    (KR) ................. 10-2006-0079155

(51) Int. Cl.
*C07C 5/367* (2006.01)
*B01J 23/40* (2006.01)

(52) U.S. Cl. ................ 585/431; 585/434; 502/326; 502/327; 502/328

(58) Field of Classification Search ............. 585/431, 585/434; 502/326, 327, 328
See application file for complete search history.

(56) References Cited

U.S. PATENT DOCUMENTS

| | | |
|---|---|---|
| 3,531,543 A | 9/1970 | Clippinger et al. |
| 4,506,032 A | 3/1985 | Imai et al. |
| 5,012,024 A | 4/1991 | Sikkenga et al. |
| 5,073,670 A | 12/1991 | Sikkenga et al. |
| 5,118,892 A | 6/1992 | Sikkenga et al. |
| 5,189,234 A | 2/1993 | Amelse |
| 5,396,007 A | 3/1995 | Kyuko et al. |
| 5,401,705 A | 3/1995 | Amelse |
| 5,401,892 A | 3/1995 | Sikkenga et al. |
| 6,388,158 B1 | 5/2002 | Perego et al. |
| 6,472,576 B1 | 10/2002 | Bergstrom et al. |

FOREIGN PATENT DOCUMENTS

| | | |
|---|---|---|
| CA | 2 166 522 A1 | 7/1997 |
| EP | 1 069 102 A1 | 1/2001 |
| GB | 435 254 A | 9/1935 |
| GB | 472 538 A | 9/1937 |
| JP | 2001 2778821 A | 10/2001 |
| KR | 10-2005-0054559 | 6/2005 |
| WO | W 00/34212 A | 6/2000 |

*Primary Examiner*—Thuan Dinh Dang
(74) *Attorney, Agent, or Firm*—Nixon & Vanderhye P.C.

(57) ABSTRACT

Disclosed herein is a process of producing high purity and high yield dimethylnaphthalene by dehydrogenating a dimethyltetralin isomer using a metal catalyst for dehydrogenation. The metal catalyst contains a carrier selected from alumina ($Al_2O_3$), silica ($SiO_2$), a silica-alumina mixture and zeolite. The metal catalyst also contains 0.05 to 2.5% by weight of platinum (Pt), 0.1 to 3.0% by weight of tin (Sn) or indium (In), 0.5 to 15.0% by weight of at least one selected from the group consisting of potassium (K), magnesium (Mg) and cesium (Cs), 0.3 to 3.0% by weight of chlorine, and 0.01 to 3.0 % by weight of zinc (Zn) or gallium (Ga) as active components based on an element weight of the final catalyst.

5 Claims, No Drawings

DEHYDROGENATION PROCESS OF DIMETHYLNAPHTHALENE USING METAL CATALYST

BACKGROUND OF THE INVENTION

1. Field of the Invention

The present invention relates to a process of producing high purity and high yield dimethylnaphthalene (DMN) by dehydrogenating a dimethyltetralin (DMT) isomer using a metal catalyst for dehydrogenation. More particularly, the present invention pertains to a metal catalyst for dehydrogenation that is used to dehydrogenate hydrocarbons having 5 to 20 carbon atoms, and a process of producing dimethylnaphthalene using the same catalyst. The metal catalyst contains a carrier selected from the group consisting of alumina ($Al_2O_3$), silica ($SiO_2$), a silica-alumina mixture and zeolite; and 0.05 to 2.5 wt % platinum (Pt); 0.1 to 3.0 wt % tin (Sn) or indium (In); 0.5 to 15.0 wt % at least one selected from the group consisting of potassium (K), magnesium (Mg) and cesium (Cs); 0.3 to 3.0 wt % chlorine as active components calculated on elemental basis of the final catalyst. Additionally 0.01 to 3.0 wt % zinc (Zn) or gallium (Ga) as active components calculated on elemental basis of the final catalyst is immersed in the metal catalyst.

2. Description of the Related Art

Known Arts regarding dehydrogenation processes using a catalyst for dehydrogenation are as follows.

U.S. Pat. No. 3,531,543 discloses dehydrogenating hydrocarbons with a catalyst comprising platinum and tin in an alumina carrier. U.S. Pat. No. 4,506,032 suggests the catalyst comprising further halogen component to desirably improve reactivity and selectivity.

Additionally, U.S. Pat. No. 5,012,024 suggests dehydrogenating hydrocarbons with a catalyst containing the palladium (Pd) component in an alumina ($Al_2O_3$) carrier, and the dehydrogenation reaction temperature is 200 to 300° C., and the pressure is 0.5 to 5.1 $kgf/cm^2$.

Furthermore, U.S. Pat. No. 5,396,007 suggests the dehydrogenating process using a catalyst for dehydrogenation containing platinum (Pt) and palladium (Pd) components as the active component in an activated carbon as the carrier, and at least one of nitrogen ($N_2$), argon (Ar) and helium (He) is added with raw materials at the pressure of 0.1 to 10 $kgf/cm^2$ and the reaction temperature of 200 to 350° C. in the gas phase. Additionally, U.S. Pat. No. 5,189,234 suggests a dehydrogenating process of organic compounds having 2 to 50 carbon atoms with a catalyst consisting of platinum (Pt) or palladium (Pd) immerged into alumina ($Al_2O_3$) in an alkaline solution of alkali metal salts, and the reaction temperature is 200 to 350° C., and the pressure is 10 $kgf/cm^2$.

The present inventors have conducted studies on the catalyst for dehydrogenating saturated hydrocarbons having 11 carbon atoms or more disclosed in Korean Patent Laid-Open Publication No. 10-2005-0054559, showing that the said dehydrogenation reaction is preferably performed in either liquid or gas phase. With respect to the reaction condition, the catalyst for dehydrogenation is useful under the following condition. Preferably, the temperature of the liquid phase reaction is 180 to 350° C. and the pressure is high enough to maintain the liquid phase of the reactants, and the temperature of the gas phase reaction is 250 to 550° C. and the pressure is low enough to maintain the gas phase of the reactants.

However, the activated carbon and the alumina as the carrier of the catalyst are used in the above-mentioned processes, and the dehydrogenation ability is improved by changing structural physical properties of the active component or the carrier. However, when used at a high temperature and pressure for a long time, there are still some problems unsolved such as the changes in the structural physical properties of the carrier, the reduction of area of the active component, the deterioration of performance of the catalyst, shortened life span and the reduction of selectivity of dehydrogenation. Furthermore, mechanical strength and thermal stability are poor due to damages to the catalyst resulting from a change in pressure of the incoming gas.

SUMMARY OF THE INVENTION

It is an object of the present invention to provide a process for producing dimethylnaphthalene to improve the deterioration of activity, conversion ratio and yield due to the usage of a platinum catalyst for dehydrogenation under high temperature and pressure for a long time. Accordingly, the present invention provides a novel complex metal catalyst for dehydrogenation that includes complex metal catalyst components containing 0.5 to 15.0% by weight of at least one selected from the group consisting of potassium (K), magnesium (Mg) and cesium (Cs), and 0.01 to 3.0% by weight of zinc (Zn) or gallium (Ga). Furthermore, the present invention provides a process of producing high purity and high yield dimethylnaphthalene using the catalyst under high temperature and pressure.

The present invention relates to a metal catalyst for dehydrogenating hydrocarbons having 5 to 20 carbon atoms, and the dehydrogenation reaction using the same catalyst. Specifically, the present invention relates to a process of producing high purity and a high yield dimethylnaphthalene (hereinafter, referred to as 'DMN') by dehydrogenating a dimethyltetralin (hereinafter, referred to as 'DMT') isomer using the metal catalyst for dehydrogenation.

In an embodiment of the present invention, there are provided a metal catalyst for dehydrogenation, and a process of producing dimethylnaphthalene using the same. The metal catalyst contains a carrier selected from the group consisting of alumina ($Al_2O_3$), silica ($SiO_2$), a silica-alumina mixture and zeolite, and 0.05 to 2.5% by weight of platinum (Pt), 0.1 to 3.0% by weight of tin (Sn) or indium (In), 0.5 to 15.0% by weight of at least one selected from the group consisting of potassium (K), magnesium (Mg) and cesium (Cs), 0.3 to 3.0% by weight of chlorine, and 0.01 to 3.0% by weight of zinc (Zn) or gallium (Ga) as active components based on an element weight of the final catalyst.

According to another embodiment of the present invention, the said metal catalyst may further contain 0 to 4.0% by weight of sulfur calculated on the elemental basis of the final catalyst.

According to another embodiment of the present invention, the dehydrogenation is performed under a liquid phase, 10 to 30 $kgf/cm^2$ of pressure, 2 to 30 $hr^{-1}$ of weight hourly space velocity and 300 to 450° C. of reaction temperature.

DESCRIPTION OF THE PREFERRED EMBODIMENTS

Hereinafter, the present invention will be described in detail.

A catalyst should enhance the rate of thermodynamic equilibrium and suppress the generation of structural isomers by increasing dehydrogenation rate. In addition, the catalyst should have the ability to suppress the thermal decomposition of hydrocarbons that may be generated during the process of dehydrogenation, and have continuous stability of activity under the industrial condition. The stability refers to the rate of the activity according to the time elapse and the changes in selectivity, and the changes in the rate of activity occured when the catalyst is regenerated and re-used after a predetermined time. Therefore a catalyst with lower rate of change is considered to be stable, and increases the time to continuously use the catalyst, that is, the economic life span of the catalyst.

The factors to reduce the stability of the catalyst may include the occurrence of carbon precipitation(coking) which causes reductions in the contact efficiency of reactants on an active surface and the contact area of reactants with the active surface due to sintering between active components caused by various reasons during the catalyst regeneration process, and the change of treatment conditions of the catalyst itself under the industrial conditions.

Occasionally the factors may include the catalyst loss into the reactants resulting from the breakage of the catalyst, and the partial loss of catalyst components.

Basically, the catalyst according to the present may include one of chemical compounds such as alumina ($Al_2O_3$), silica ($SiO_2$), a silica-alumina mixture and Zeolite as a main component carrier, and active metal is immersed in the main component carrier. Preferably, alumina ($Al_2O_3$) is used as the carrier.

A carrier may be produced by using a known process such as precipitation, sol-gel and ion exchanging. The materials have desirable physical properties through a shaping process and a sintering process. Preferably, the sol-gel process may be used, or hydrocarbon oil may be additionally used as a pore forming agent to produce the carrier material.

The pore structure of the catalyst according to the present invention is measured using a nitrogen adsorption process. The pore volume of the catalyst is 0.4 to 1.0 cc/g, the average pore size of the catalyst is 200 to 3000 Å, the nitrogen adsorption surface area of the catalyst is 25 to 150 $m^2/g$. The above-mentioned pore characteristics are determined during a process of producing the carrier material. Particularly, desirable features may be obtained by controlling a mixing ratio and a mixing characteristic at an initial stage of manufacturing the carrier and during drying and sintering processes.

The alumina manufactured has a γ-, θ-, or α-type of crystal structure. The surface area of the alumina is 5 to 250 $m^2/g$, and preferably 25 to 150 $m^2/g$.

In the present invention, with respect to the addition of platinum (Pt), tin (Sn), potassium (K), magnesium (Mg), gallium (Ga), zinc (Zn) or cesium (Cs), commercially usable water-soluble or resoluble compounds containing the active components may be sequentially added in the gas phase or liquid phase in the course of producing the carrier. Alternatively, the above components may be added after the thermally stable carrier is produced, and then the drying process and the sintering process may be performed, so that the above components are contained in the catalyst.

The catalyst of the present invention contains 0.05 to 2.5% by weight of platinum (Pt), 0.1 to 3.0% by weight of tin (Sn) or indium (In), 0.5 to 15.0 % of at least one selected from the group consisting of potassium (K), magnesium (Mg) and cesium (Cs), and 0.01 to 3.0% by weight of zinc (Zn) or gallium (Ga) as main active components. In the catalyst, elements are finely dispersed in the carrier.

Meanwhile, the catalyst containing 0.05 to 2.0% by weight of platinum (Pt), 0.05 to 1.0% by weight of tin (Sn), 0.05 to 3.0% by weight of alkali metal or alkali earth metal, and 0.0 to 2.0% by weight of chlorine as the main active components used during the process of dehydrogenating saturated hydrocarbons having 11 or more carbon atoms was invented by the present inventors. However, the components constituting the former catalyst are different from those of the catalyst of the present invention. According to the catalyst of the present invention, the amount of tin is increased and that of potassium (K), magnesium (Mg) or cesium (Cs) is also increased. The catalyst of the present invention also contains zinc (Zn) or gallium (Ga). As a result, the mechanical strength and thermal stability are desirable at high temperature and pressure, and the problems of reductions in activity, selectivity, and conversion rate of the catalyst are improved.

In the process of immersing the active component in the catalyst, the water-soluble or resoluble complex that contains the active component comes into contact with the carrier material in conjunction with a predetermined acid solution and water. It is preferable to use a weak acid (hydrogen ion concentration of 0.5 to 7.0) as the acid solution. A strong acid such as hydrochloric acid, nitric acid or a sulfuric acid may be used after controlling its concentration.

According to the present invention, the precursor of the platinum component may include chloroplatinic acids, ammonium chloroplatinates, bromoplatinic acids, chloroplatinic hydrates, organic amine platinum chlorides, platinum carbonyl salts or acids, and platinum nitrate salts or acids. Among them, it is preferable to use the chloroplatinic acids. Preferably, the precursor and the weak acid are immersed in the carrier material using a known impregnation process (adsorption process).

Meanwhile, it is preferable to perform the process of impregnation of the solution containing platinum after the production of the carrier material is completed, that is, after completing the sintering treatment process at 400 to 900° C. for 1 to 60 hours while a mixing ratio of dry air to steam is 0 to 200, in order to prevent fine platinum metal particles from being agglomerated at high temperature.

The amount of the platinum component (Pt) is preferable to use 0.05 to 2.5% by weight based on the element weight of the final catalyst. If the amount of the platinum component is less than 0.05% by weight, the selectivity and the conversion ratio are reduced due to the deterioration of the activity of the catalyst. If the amount is more than 2.5% by weight, the economic efficiency is reduced due to the increase in the production cost of the catalyst.

Materials containing tin include stannous chloride, stannic chloride, tin halide and hydrates thereof, stannic sulfate, tartrate, and tin nitrate. Preferably, it is preferable to use a tin chloride-based chlorine compound or a nitrate ion. The material containing tin may be added during the production of the carrier, before and after the carrier material is shaped, or before a gelation process or a dry process in the case that the aluminum sol is used. Alternatively, after the carrier is produced so as to have a predetermined shape and to be thermally stable, the process of impregnation may be performed at room temperature. After the tin compound is added to the carrier in an aqueous solution form, the process of sintering is performed at a temperature of 200 to 1200° C. for 1 to 60 hours so that the ratio of dry air to steam is 0 to 200 to produce the carrier material. The final catalyst contains 0.1 to 3.0% by weight of tin (Sn) element.

At least one metal selected from the group of metals consisting of potassium (K), magnesium (Mg) and cesium (Cs) may be impregnated in the carrier material before and after the carrier material is sintered at a high temperature of 500° C. or more, before and after other components are added to the carrier material, or at the same time other components are added to the carrier material. Preferably, the process of impregnation is performed simultaneously with the process of immersion of the platinum component in aqueous solution in the carrier. After the above-mentioned components are maintained at normal temperature for 1 to 4 hours, they are agitated or swirled in a dry air atmosphere at 80 to 90° C. for 0.5 to 4 hours, dried under lax conditions of a gas hourly space velocity (GHSV) of 10 to 3000 $hr^{-1}$ and 150° C. for 2 to 24 hours, and sintered at 300 to 700° C. for 2 to 48 hours so that the mixing ratio of dry air to steam is 0 to 100 and the gas hourly space velocity is 10 to 3000 $hr^{-1}$. Thereby, the immersion process of the components is performed.

The zinc (Zn) or gallium (Ga) component may be immesred in the gas phase or liquid phase process during or before the production of the carrier material, or during or after other catalyst compositions are added. The components contain nitrates, organic amine salts, bromo salts, or chlorides. Preferably, the components contain nitrates. After the components are maintained at normal temperature for 1 to 4 hours, they are agitated or swirled in a dry air atmosphere at 80 to 90° C. for 0.5 to 4 hours, dried under lax conditions of a gas hourly space velocity of 10 to 3000 $hr^{-1}$ and at 150° C. for 2 to 24 hours, and sintered at 300 to 700° C. for 2 to 48 hours so that the mixing ratio of dry air to steam is 0 to 100 and the gas hourly space velocity is 100 to 3000 $hr^{-1}$. Thereby, the immersion process of the components is performed.

The chlorine ($Cl_2$) component may be added in the predetermined process during or before the production of the carrier material, or during or after other catalyst compositions are added. Chlorine may be added to water-soluble or resoluble salts of additives of the catalyst, or a predetermined acid containing chlorine, such as a hydrochloric acid, may come into contact with the catalyst composition in a gas phase or a liquid phase to control the amount of chlorine in the catalyst. In the present invention, the final catalyst contains 0.3 to 3.0% by weight of chlorine element.

Once the immersion process of the active components is completed, the active components are fixed to the carrier and then subjected to the following process, so that the resulting substance is activated to have a catalytic performance.

The carrier to which the active components are fixed is subjected to a final sintering process at 300 to 700° C. for 1 to 48 hours so that the mixing ratio of dry air to steam is 0 to 50 and the gas hourly space velocity is 100 to 3000 $hr^{-1}$.

A predetermined reduction process is required to be performed in order to assure desirable activity of the catalyst of the present invention during the dehydrogenation process of hydrocarbons. The reduction may be performed during or before the dehydrogenation process. If the catalyst is reduced during the process while hydrogen having 99.9% of purity is blown at the GHSV of 0 to 2000 $hr^{-1}$ at 550 to 700° C. for 1 to 24 hours, a desirable activity can be obtained.

Furthermore, the catalyst of the present invention may further contain sulfur. During the production of the catalyst, a small amount of organic sulfur compound may be fixed to the catalyst. Alternatively, after the catalyst is produced, 0 to 10,000 ppm of organic sulfur may be injected into the reaction gas to provide a sulfur component to the catalyst, or the catalyst may comes into contact with sulfur during the reaction. In order to assure optimum activity of the catalyst of the present invention, the amount of sulfur varies according to the reaction condition at a range of 0 to 4% by weight based on the amount of the catalyst after the reaction. If the catalyst contains sulfur, the generation of coke is maximally suppressed during the reaction to prevent the activity of the catalyst from being reduced. If the amount of sulfur in the catalyst is more than 4% by weight, it has a mere effect to improve the activity of sulfur.

Meanwhile, for a long-term usage of the catalyst of the present invention, carbon precipitates may be periodically removed, or the catalyst may be treated using steam after the reaction in order to improve the activity. The carbon precipitates may be removed using a combustion process in a controlled oxygen and nitrogen atmosphere, or the carbon product may be slowly gasified using steam in controlled nitrogen and air atmosphere to remove the carbon precipitates. In connection with this, in order to improve stability of the activity of the catalyst, the chlorine component or the sulfur component may be added.

The dehydrogenation process of the present invention may be stepwise or continuously performed. Preferably, the dehydrogenation is continuously performed.

More detailed description of the process of dehydrogenating dimethylnaphthalene according to the present invention is as follows. First, the catalyst produced in the mentioned-above processes from the dimethyltetralin isomer mixture produced in a process of synthesizing dimethyltetralin is charged in a reactor in either a fixed or a fluidized bed method, and then is dehydrogenated in the reactor at temperature of 300 to 500° C. and pressure of 10 to 30 $kgf/cm^2$ to synthesize dimethylmaphthalene. It is preferable that the temperature of the reactor be at 350 to 450° C. and the pressure be 10 to 20 $kgf/cm^2$ during the reaction. A weight hourly space velocity (WHSV) is 2 to 30 $hr^{-1}$. Preferably, the reaction is performed with the weight hourly space velocity of 10 to 20 $hr^{-1}$.

A better understanding of the present invention may be obtained in light of the following Examples, which may be modified in various ways, but are not to be construed to limit the present invention.

The process of producing the catalyst for dehydrogenation according to the present invention is disclosed in the following Comparative examples and Examples. The conversion ratio and the selectivity according to the present invention were calculated using the following equations.

The gas chromatography analysis was performed after the reaction in the pilot reactor.

$$\text{conversion ratio}[\%] = \frac{([\text{the amount of 1, 5-}DMT\text{ before reaction}] - [\text{the amount of 1, 5-}DMT\text{ after reaction}])}{[\text{the amount of 1, 5-}DMT\text{ before reaction}]} \times 100$$

$$\text{selectivity}[\%] = \frac{[\text{the amount of produced 1, 5-}DMN]}{([\text{the amount of 1, 5-}DMT\text{ before reaction}] - [\text{the amount of 1, 5-}DMT\text{ after reaction}])} \times 100$$

Comparative Example 1

In order to show advantages of the present invention, a comparative catalyst was produced according to U.S. Pat. No. 5,189,234. Alumina was used as the carrier, and 0.60% by weight of platinum (Pt) was immersed in the carrier in conjunction with the weak acid using a known impregnation process and 0.79% by weight of chlorine ($Cl_2$) was immersed in the aqueous solution of the alkali metal salt, and 1.0% by weight of sodium (Na) was used as the alkali metal. From the excessive amount of aqueous solution of the alkali metal salt, remaining halogen compounds were removed and the processes of sintering and the drying were performed to produce the catalyst A.

In order to show advantages of the present invention, a comparative catalyst was produced according to Korean Patent Laid-Open Publication No. 10-2005-0054559. Alumina was used as the carrier, and 0.5% by weight of platinum (Pt), 0.5% by weight of tin (Sn), 0.5% by weight of potassium (K) that was the alkali metal component, and 1.0% by weight of chlorine ($Cl_2$) was immersed as the active components. The remaining halogen compounds were removed from the aqueous solution of the alkali metal salt. The drying process was performed at 150° C. for 2 hours, and the sintering process was conducted at 600° C. to produce the catalyst B.

Example 1

A combined catalyst containing tin was used. First, after 12.0 g of tin chlorides ($SnCl_2$) was partially dissolved in 398 ml of water, 8.5 ml of the hydrochloric acid was added to completely dissolve the tin chlorides. Alumina was immersed in the solution for 4 hours. Alumina in which the tin component was immersed was dried at 150° C. for 2 hours or more under 100 $hr^{-1}$ of the dry gas hourly space velocity (GHSV), and then sintered at 680° C. for 3 hours under 1000 $hr^{-1}$ GHSV to produce the catalyst. The carrier containing tin was added to 357 ml of the chloroplatinic acid aqueous solution (the concentration of platinum was 0.0055 g Pt/ml) to immerse the platinum component. Subsequently, a drying process was performed using dry air at 150° C. for 2 hours, a sintering process was performed at 600° C. for 2 hours, and the solution in which 742 ml of the aqueous solution containing 9.05 g of potassium nitrate was mixed with the 2% hydrochloric acid were impregnated. Next, a drying process was performed using dry air at 150° C. for 2 hours, and a sintering process was performed at 600° C. for 2 hours. Zinc and other compositions were simultaneously added during the production of the carrier material, and the immersion of zinc was then performed. Nitrates were used as the substance containing the zinc component. The resulting catalyst was called the catalyst C. All the components were uniformly immersed in the catalyst particles. The resulting catalyst contained 0.5% by weight of platinum, 2.0% by weight of tin, 1.0% by weight of potassium, 0.1% by weight of zinc, and 0.7% by weight of chlorine based on the element weight in the final catalyst.

Comparative Examples 2 to 5 and Examples 2 to 5

In the present Examples and Comparative examples, the dehydrogenation abilities of the catalyst C of Example 1 and the catalyst A of Comparative example 1 were compared using the laboratory reactor.

After the catalysts C and A were charged in the reactor to form the fixed bed, the dimethyltetralin isomer was dehydrogenated under the conditions including the reaction pressure of 15 kgf/$cm^2$, the weight hourly space velocity (hereinafter, referred to as "WHSV") of 20 $hr^{-1}$, and the temperature of 300 to 450° C. to generate the dimethylnaphthalene isomer. The composition, the selectivity, and the conversion ratio of the dimethylnaphthalene isomer were obtained, and the results are described in the following Table 1.

TABLE 1

| | | Composition of products (%) Temperature (° C.) | | | | | | | |
|---|---|---|---|---|---|---|---|---|---|
| | | 300° C. | | 350° C. | | 400° C. | | 450° C. | |
| Composition of reactants (%) | | Com. example 2 | Example 2 | Comp. example 3 | Example 3 | Com. example 4 | Example 4 | Com. example 5 | Example 5 |
| Low boiling point | 0.97 | 1.01 | 0.95 | 0.92 | 0.65 | 0.89 | 1.19 | 0.86 | 0.8 |
| 5-OTP-2 | 1.19 | 1.23 | 1.19 | 1.23 | 1.08 | 1.19 | 1.11 | 1.09 | 0.90 |
| 1,5-DMT | 90.14 | 8.04 | 2.03 | 5.02 | 0.98 | 2.01 | 0.03 | 1.67 | 0.03 |
| 1,6-DMT 2,5-DMT | 2.96 | 1.01 | 0.35 | 0.86 | 0.06 | 0.69 | 0 | 0.06 | 0 |
| Other DMTs | 0.84 | 0.41 | 0.42 | 0.55 | 0.02 | 0.57 | 0 | 0.02 | 0 |
| 2,6-DMN | 0 | 0.31 | 0.68 | 0.71 | 1.01 | 1.03 | 1.26 | 1.31 | 1.36 |
| 1,6-DMN | 0 | 1.05 | 1.23 | 1.53 | 1.92 | 1.47 | 1.64 | 1.97 | 2.01 |
| 1,5-DMN | 0 | 81.68 | 88.03 | 82.74 | 88.56 | 85.06 | 89.94 | 85.97 | 89.99 |
| Other DMNs | 0.22 | 1.8 | 2.14 | 2.46 | 2.98 | 2.63 | 2.71 | 3.03 | 2.85 |
| High boiling point | 3.68 | 3.64 | 2.98 | 3.98 | 2.74 | 4.46 | 2.12 | 4.02 | 2.12 |
| Total (%) | 100 | 100 | 100 | 100 | 100 | 100 | 100 | 100 | 100 |
| Conversion ratio (%) | | 91.08 | 97.74 | 94.43 | 98.91 | 97.77 | 99.96 | 98.88 | 99.96 |
| Selectivity (%) | | 99.40 | 99.90 | 97.20 | 99.32 | 96.51 | 99.81 | 97.17 | 99.86 |

Examples 6 to 10

The dimethyltetralin isomer was dehydrogenated using the catalyst C of Example 1 under the conditions including the reaction temperature of 450° C., the WHSV of 20 $hr^{-1}$, and the reaction pressure of 10 to 30 kgf/$cm^2$ to produce the dimethylnaphthalene isomer. The composition, the selectivity, and the conversion ratio of the dimethylnaphthalene isomer were obtained, and the results are described in the following Table 2.

TABLE 2

| Composition of reactants (%) | | Composition of products (%) | | | | |
|---|---|---|---|---|---|---|
| | | Example 6 10 kgf/cm$^2$ | Example 7 15 kgf/cm$^2$ | Example 8 20 kgf/cm$^2$ | Example 9 25 kgf/cm$^2$ | Example 10 30 kgf/cm$^2$ |
| Low boiling point | 3.76 | 2.94 | 3.21 | 3.49 | 3.71 | 3.83 |
| 5-OTP-2 | 1.56 | 1.47 | 1.52 | 1.58 | 1.54 | 1.56 |
| 1,5-DMT | 85.46 | 0.76 | 0.01 | 0.78 | 1.01 | 1.78 |
| 1,6-DMT | 5.26 | 0.19 | 0.01 | 0.13 | 0.62 | 1.45 |
| 2,5-DMT | | | | | | |
| Other DMTs | 3.45 | 0.02 | 0 | 0.41 | 0.94 | 1.23 |
| 2,6-DMN | 0 | 1.67 | 2.66 | 1.75 | 1.71 | 1.29 |
| 1,6-DMN | 0.01 | 4.04 | 4.11 | 3.49 | 1.99 | 1.51 |
| 1,5-DMN | 0 | 84.56 | 85.12 | 84.26 | 84.11 | 83.14 |
| Other DMNs | 0.09 | 4.23 | 3.01 | 3.98 | 3.95 | 3.61 |
| High boiling point | 0.41 | 0.12 | 0.15 | 0.13 | 0.42 | 0.50 |
| Total (%) | 100 | 100 | 100 | 100 | 100 | 100 |
| Conversion ratio (%) | | 99.11 | 99.98 | 99.08 | 98.81 | 97.91 |
| Selectivity (%) | | 99.83 | 99.84 | 99.50 | 99.59 | 99.35 |

Examples 11 to 15

The dimethyltetralin isomer was dehydrogenated using the catalyst C of Example 1 under the conditions including the reaction temperature of 300° C., the WHSV of 20 hr$^{-1}$, and the reaction pressure of 10 to 30 kgf/cm$^2$ to generate the dimethylnaphthalene isomer. The composition, the selectivity, and the conversion ratio of the dimethylnaphthalene isomer were obtained, and the results are described in Table 3.

Comparative Examples 7 to 9 and Examples 16 to 18

The dimethyltetralin isomer was dehydrogenated using the catalyst B of Comparative example 2 and the catalyst C of Example 1 under the liquid phase reaction conditions including the pressure of 15 kgf/cm$^2$, the WHSV of 20 hr$^{-1}$, and the reaction temperature of 350 to 450° C. to generate the dimethylnaphthalene isomer. The composition, the selectivity, and the conversion ratio of the dimethylnaphthalene isomer were obtained, and the results are described in Table 4.

TABLE 3

| Composition of reactants (%) | | Composition of products (%) | | | | |
|---|---|---|---|---|---|---|
| | | Example 11 10 kgf/cm$^2$ | Example 12 15 kgf/cm$^2$ | Example 13 20 kgf/cm$^2$ | Example 14 25 kgf/cm$^2$ | Example 15 30 kgf/cm$^2$ |
| Low boiling point | 2.87 | 2.82 | 3.16 | 3.31 | 3.56 | 3.94 |
| 5-OTP-2 | 1.01 | 1.06 | 1.13 | 1.19 | 1.17 | 1.21 |
| 1,5-DMT | 87.59 | 0.76 | 1.56 | 4.76 | 5.78 | 6.04 |
| 1,6-DMT | 4.06 | 0.78 | 0.94 | 1.93 | 2.01 | 3.14 |
| 2,5-DMT | | | | | | |
| Other DMTs | 2.15 | 0.12 | 0.29 | 1.43 | 1.23 | 2.01 |
| 2,6-DMN | 0.01 | 1.11 | 1.07 | 0.56 | 0.52 | 0.23 |
| 1,6-DMN | 0.13 | 2.76 | 2.84 | 1.41 | 1.06 | 0.74 |
| 1,5-DMN | 0 | 85.12 | 84.57 | 82.43 | 81.13 | 80.14 |
| Other DMNs | 0.18 | 3.41 | 3.21 | 2.13 | 2.75 | 1.74 |
| High boiling point | 2.00 | 2.06 | 1.23 | 0.86 | 0.79 | 0.81 |
| Total (%) | 100 | 100 | 100 | 100 | 100 | 100 |
| Conversion ratio (%) | | 99.13 | 98.21 | 94.56 | 93.40 | 93.10 |
| Selectivity (%) | | 98.03 | 98.30 | 99.51 | 99.16 | 98.27 |

TABLE 4

| Composition of reactants (%) | | Composition of products (%) Temperature (° C.) | | | | | |
|---|---|---|---|---|---|---|---|
| | | 350 | | 400 | | 450 | |
| | | Com. example 7 | Example 16 | Com. example 8 | Example 17 | Com. example 9 | Example 18 |
| Low boiling point | 0.97 | 0.99 | 0.65 | 0.73 | 1.19 | 0.48 | 0.80 |
| 5-OTP-2 | 1.19 | 1.44 | 1.08 | 1.01 | 1.11 | 1.03 | 0.90 |
| 1,5-DMT | 90.14 | 7.34 | 0.98 | 5.47 | 0.03 | 4.52 | 0.03 |
| 1,6-DMT | 2.96 | 2.64 | 0.06 | 1.29 | 0.00 | 1.64 | 0.00 |
| 2,5-DMT | | | | | | | |
| Other DMTs | 0.84 | 0.65 | 0.02 | 0.38 | 0.00 | 0.65 | 0.00 |
| 2,6-DMN | 0 | 0.22 | 1.01 | 0.19 | 1.26 | 0.24 | 1.36 |
| 1,6-DMN | 0 | 0.98 | 1.92 | 0.48 | 1.64 | 0.61 | 2.01 |
| 1,5-DMN | 0 | 80.15 | 88.56 | 82.24 | 89.94 | 82.84 | 89.99 |
| Other DMNs | 0.22 | 1.61 | 2.98 | 3.21 | 2.71 | 2.99 | 2.85 |
| High boiling point | 3.68 | 4.77 | 2.74 | 5.70 | 2.12 | 6.01 | 2.12 |
| Total(%) | 100 | 100 | 100 | 100 | 100 | 100 | 100 |
| Conversion ratio (%) | | 91.85 | 98.91 | 93.93 | 99.96 | 94.98 | 99.96 |
| Selectivity (%) | | 96.70 | 99.32 | 97.13 | 99.81 | 96.75 | 99.86 |

Examples 19 to 20

The catalyst B of Comparative example and the catalyst C of Example 1 were left in the reactor under the conditions including the reaction temperature of 450° C., the pressure of 15 Kgf/cm², and the WHSV of 20 hr⁻¹ for a long time. Performance of the catalyst for dehydrogenation was tested, and the results are described in the following Table 5.

TABLE 5

| | | | Total reaction time | | | |
|---|---|---|---|---|---|---|
| | | | 2 days | 7 days | 15 days | 30 days |
| Evaluation of performance of catalyst | C | Conversion ratio (%) | 99.96 | 99.88 | 99.83 | 99.80 |
| | | Selectivity | 99.86 | 99.86 | 99.89 | 99.88 |
| | B | Conversion ratio (%) | 94.98 | 93.56 | 91.41 | 81.90 |
| | | Selectivity | 96.75 | 96.40 | 94.72 | 94.40 |

In dehydrogenation of dimethylnaphthalene performed with a catalyst produced according to the present invention, the selectivity and the conversion ratio are excellent, and it assures excellent efficiency even though a small amount of catalyst is used. Additionally, with a very stable performance of the catalyst according to a reaction time, it is economically very useful in that the fixed investment cost and the production cost are reduced.

What is claimed is:

1. A process of producing dimethylnaphthalene comprising:
    dehydrogenating a dimethyltetralin isomer to produce dimethylnaphthalene in the presence of a metal catalyst for dehydrogenation,
    wherein the carrier of the metal catalyst is alumina ($Al_2O_3$), silica ($SiO_2$), a silica-alumina mixture, or zeolite, and
    the metal catalyst also contains 0.05 to 2.5% by weight of platinum (Pt), 0.1 to 3.0% by weight of tin (Sn) or indium (In), 0.5 to 15.0% by weight of at least one selected from the group consisting of potassium (K), magnesium (Mg), and cesium (Cs), 0.3 to 3.0% by weight of chlorine, and 0.01 to 3.0% by weight of zinc (Zn) or gallium (Ga) as active components based on a weight of the resulting catalyst.

2. The process of producing dimethylnaphthalene according to claim 1, wherein the metal catalyst further contains 0 to 4.0% by weight of sulfur based on the element weight of the final catalyst.

3. The process of producing dimethylnaphthalene according to claim 1, wherein a pressure is 10 to 30 kgf/cm² during the dehydrogenating.

4. The process of producing dimethylnaphthalene according to claim 1, wherein a weight hourly space velocity is 2 to 30 hr⁻¹ during the dehydrogenating.

5. The process of producing dimethylnaphthalene according to claim 1, wherein a temperature is 300 to 450° C. during the dehydrogenating.

* * * * *